(12) United States Patent
Hennenfent

(10) Patent No.: US 6,409,688 B1
(45) Date of Patent: Jun. 25, 2002

(54) RECTAL GLOVE

(76) Inventor: Bradley R. Hennenfent, 454 Summer Dr. NE., Atlanta, GA (US) 30328

( * ) Notice: Subject to any disclaimer, the term of this patent is extended or adjusted under 35 U.S.C. 154(b) by 0 days.

(21) Appl. No.: 09/439,447

(22) Filed: Nov. 15, 1999

(51) Int. Cl.[7] .................................................. A61H 1/00
(52) U.S. Cl. ............................. 601/18; 601/15; 601/19; 601/112; 601/113; 601/131
(58) Field of Search ............................... 601/15, 18, 19, 601/112, 113, 131; 2/16, 160; 222/78; 401/7

(56) References Cited

U.S. PATENT DOCUMENTS

| | | |
|---|---|---|
| 3,701,604 A | 10/1972 | Holroyd |
| 3,883,897 A | 5/1975 | Lefkowitz et al. |
| 4,903,864 A | 2/1990 | Sirhan |
| 5,045,073 A | 9/1991 | Wagner |
| 5,169,251 A | 12/1992 | Davis |
| 5,466,080 A | 11/1995 | Lee |
| 5,722,349 A | 3/1998 | Wolgamuth |

Primary Examiner—Michael A. Brown
Assistant Examiner—Lalita M. Hamilton
(74) Attorney, Agent, or Firm—Patula & Associates, P.C.

(57) ABSTRACT

A glove device for employment in the communication of medications, lubricants, or other substances is described, which is particularly useful in communicating such substances to in vivo treatment areas, such as the prostate or rectum. The glove device is preferably embodied in a substantially tactile, smooth and disposable material which contains a substance communication pathway embedded within that permits substance communication from a substance containing reservoir to an in vivo treatment site. The glove device may regulate the substance communication and may transmit greater than one substance simultaneously and in succession without removing the invention from a treatment site.

14 Claims, 2 Drawing Sheets

RECTAL GLOVE

BACKGROUND OF THE INVENTION

1. Field of the Invention

The present invention relates to devices used in the administration of rehabilitative substances, and more particularly to gloves employed for in vivo communication of medications, lubricants, or other substances to treatment areas such as the prostate, or the rectum.

2. Description of the Prior Art

Numerous medicaments in cream, ointment, and liquid bases, lubricants and other substances have been formulated for in vivo administration for treatment areas throughout a mammalian body. In many circumstances, these substances must be carefully communicated to a treatment site in order to avoid contamination of surrounding areas and inflammation at the treatment site or surrounding area. These problems are particularly significant at sensitive application sites and/or surrounding areas such as the prostate and rectum.

The prostate is a male sex gland that is important for reproduction because it produces a portion of ejaculate fluid. It is a small walnut shaped gland that is located above the rectum and surrounds the urethra at the point where the urethra connects to the bladder.

At birth, the prostate is about the size of an almond and it remains this size throughout childhood. During puberty, the prostate begins to enlarge and nearly doubles in size. At about age 45, the prostate often starts growing again and, in most cases, can continue to enlarge for the rest of a man's life. An enlarged prostate can frequently start to squeeze the urethra and interfere with the normal flow of urine causing uncomfortable symptoms such as frequent urination, sudden urges to urinate, weak interrupted urine streams, sense of incomplete bladder emptying, leakage and difficulty in starting urination. An enlarged prostate can even result in total blockage of the urethra, a very serious condition.

Several methods to compensate for an enlarged prostate are available. These procedures, however, are extremely invasive and uncomfortable. The enlargement process can also be reversed through the administration of medication, lubricants or other substances to the back of the prostate while massaging the prostate. This procedure can help improve blood flow, reduce pain, or shrink the prostate in size.

Current approaches for administering medications, lubricants or other substances to the prostate are painful, haphazard and imprecise. In this type of procedure, the doctor typically applies the substance to a gloved finger and then pokes the finger into the anus far enough to massage the substance on the back of the prostate.

This procedure is inadequate for several reasons. Much of the treatment substance is rubbed off the gloved finger upon insertion into the rectum and upon traveling to the prostate. This is wasteful and restricts the doctor from administering medication, lubricants or other substances to the prostate that may otherwise irritate the surrounding areas. Additionally, if the doctor attempts to manipulate the gloved finger that administers the treatment substance in such a manner to reduce the amount of treatment substance that is rubbed off, irritation and inflammation can occur in areas surrounding the treatment site. Further, the doctor does not know the precise amount of treatment substance that actually reaches the treatment site because much of the substance is rubbed off the gloved finger. This can result in either an overdose or underdose of medication.

No substance administration device is known that can be employed to overcome these inadequacies particular to in vivo application to treatment sites such as the prostate. In somewhat related art, glove apparatus have been provided which provide for dispensing or squirting of liquid material as the user manipulates one or more digits of the hand.

For example U.S. Pat. No. 5,466,080 issued to Lee sets forth a finger painting apparatus suitable for wearing upon the painter's hand as a substitute for a paintbrush. The glove-like apparatus includes a variety of mechanical attachments including a plurality of inverted paint bottles coupled to a corresponding plurality of flexible tubes which are connected to pad housings secured to the painter's fingertips.

U.S. Pat. No. 5,722,349 issued to Wolgamuth sets forth an ergonomic hand pet washing system which generally comprises a rubber glove, a rubber tubing secured to the glove carrying soap and water for washing, and a valve secured at the end of the rubber tubing opposite of the glove which controls the flow of soap and water. In one embodiment, the glove disclosed includes four outlet ports for the soap and water, each located at the crevice point between two fingers. In another embodiment, the glove disclosed includes an interior reservoir within the palm which communicates the soap and water to the wash site via a plurality of apertures fluidly connecting the reservoir and the palm.

U.S. Pat. No. 5,169,251 issued to Davis sets forth a hand-worn dispenser which generally comprises a glove having a self-contained palmar reservoir for storing materials to be dispensed via conduits extending from the reservoir and terminating at the fingertips where the materials are supplied and dispensed from the reservoir. The materials are discharged from the reservoir by squeezing the reservoir with the hand, or by pressing and impacting the glove directly against the object which receives the dispensed material.

U.S. Pat. No. 5,045,073 issued to Wagner sets forth a digital applicator that is worn by a single finger and a program for topical application of various medicaments. The digital applicator includes a dactyl cot formed of a tubular casing having a closed distal end and a conical medicament dispenser formed of an absorbent material such as a sponge attached to the distal end.

U.S. Pat. No. 4,903,864 issued to Sirhan sets forth a glove amusement device for squirting liquid. The glove comprises a liquid storage apparatus, a glove and an umbilical cord connecting the two and terminating at the glove fingertip. The glove produces a hard stream of liquid upon activation by a trigger mechanism also found on the glove.

U.S. Pat. No. 3,883,897 issued to Lefkowitz et al. sets forth a painting glove that may be used as a substitution of a painting brush. In one embodiment, the glove may be dipped into a paint reservoir and then used to spread paint on a work surface. In another embodiment, the glove includes a paint reservoir that allows paint to slowly flow onto the work site via conduits which terminate at each crevice between the fingers.

Lastly, U.S. Pat. No. 3,701,604 issued to Holroyd sets forth a glove device used for the manual application of a liquid over a treatment surface. The glove comprises a liquid reservoir which is connected to an absorbent material via a passage means that controls the flow of liquid. The liquid is absorbed by the absorbent material and is expressible through the material to its outer surface by manual pressure.

While the foregoing described prior art devices have provided improvements in their various arts, there remains nonetheless a continuing need in the art for a further improved, efficient, economical, and non-invasive apparatus suitable for administering treatment substances to various in vivo treatment sites, particularly to the prostate or rectum.

BRIEF SUMMARY OF THE INVENTION

A glove device for employment in the communication of medications, lubricants, or other substances is described, which is particularly useful in communicating such substances to in vivo treatment areas, such as the prostate or rectum. The glove device is preferably embodied in a substantially tactile, smooth and disposable material which contains a substance communication pathway embedded within that permits substance communication from a substance containing reservoir to an in vivo treatment site. The glove device may regulate the substance communication and may transmit greater than one substance simultaneously and in succession without removing the invention from a treatment site.

It is therefore a general object of the present invention to provide an improved glove apparatus for substance communication to internal treatment sites within a mammalian body.

Accordingly, it is an object of the present invention to provide a disposable substance communication device that may regulate the quantity of treatment substance that is administered to a treatment site.

Another object of the present invention is to provide a substance communication device which is flexible and smooth to avoid irritation and inflammation of the treatment site and/or surrounding areas.

Still another object of the present invention is to provide a substance communication device capable of communicating greater than one substance, both simultaneously and at alternate times, without removing the communication device from the treatment area.

A more particular object of the present invention is to provide a substance communication device which is sufficiently tactile so that the administering doctor can feel the treatment site to detect any abnormalities and to massage the treatment substance onto the treatment site.

A further object of the present invention is to provide a substance communication device which includes a treatment substance outlet port substantially near the point at which the glove contacts the treatment site.

A still further object of the present invention is to provide a substance communication device which includes a mechanism for regulating the time and speed of substance communication in order to avoid contamination of areas surrounding the treatment site.

Numerous other advantages and features of the present invention will become readily apparent from the detailed description of preferred embodiments of the invention, from the claims, and from the accompanying drawings in which like numerals are employed to designate like parts throughout the same.

BRIEF DESCRIPTION OF THE DRAWINGS

A fuller understanding of the foregoing may be had by reference to the accompanying drawings wherein.

DETAILED DESCRIPTION OF THE PREFERRED EMBODIMENT

Figure 1:
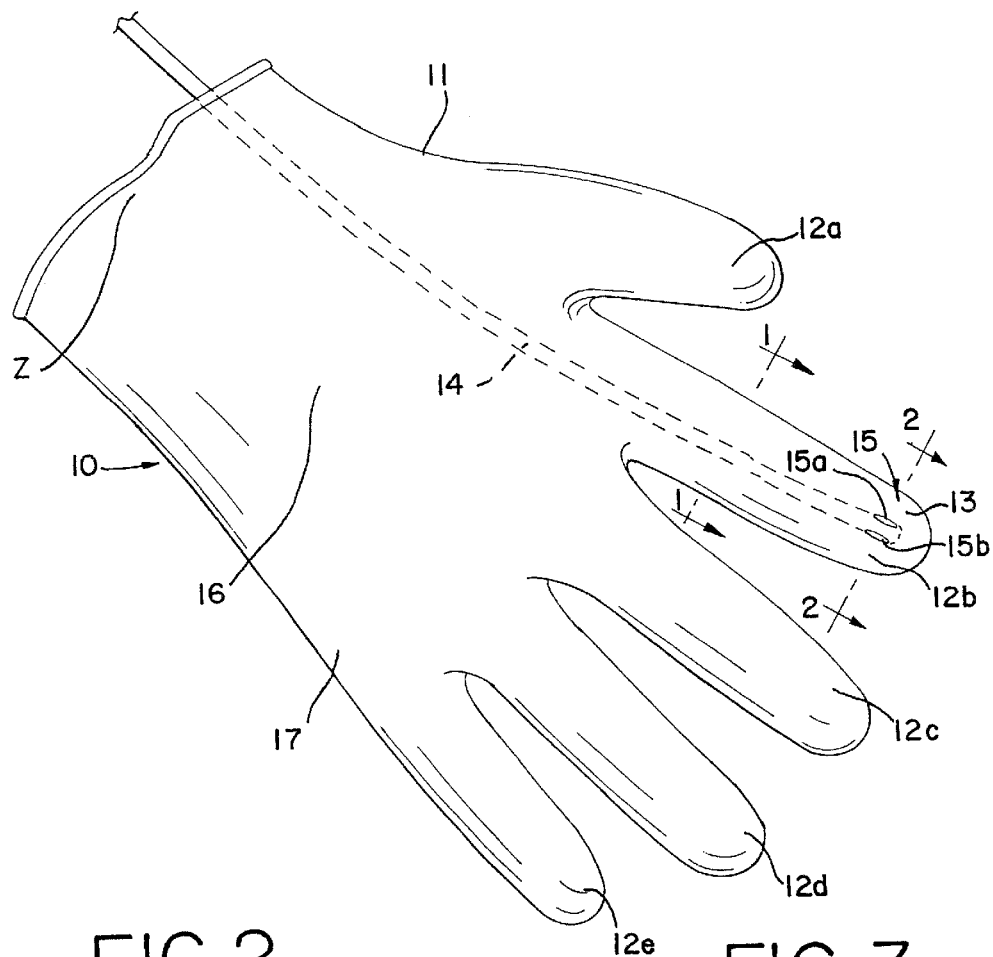
FIG. 1 sets forth a top perspective view of a substance communication device in accordance with the present invention.

While the invention is susceptible of embodiments in many different forms, there is shown in the drawings and will be described herein in detail, a preferred embodiment of the present invention. It should be understood, however, that the present disclosure is to be considered an exemplification of the principles of the invention and is not intended to limit the spirit and scope of the invention and/or claims of the embodiment illustrated.

Referring now in detail to the drawings, FIG. 1 illustrates a substance communication device according to this invention comprising a hand receiving glove body 10 having a substance communication pathway 14. The glove body 10 itself is conventionally constructed and has in addition to palm 16, a wrist portion 17, finger pockets 12b–12d, and a thumb pocket 12a. The rectal glove according to the instant invention may be substantially comprised of a disposable material and may be made available in small, medium, large and extra-large sizes in order to accommodate the size of the treating doctor's hand.

The substance communication pathway 14 is embedded within the glove body 10 and primarily functions as a conduit between the treatment substance reservoir 18 and the channel termination point 15. The substance communication pathway 14 terminates opposite the treatment substance reservoir 18 preferably at the distal end of finger pocket 12b.

Although FIG. 1 depicts the substance communication pathway traveling along the wrist portion 17, palm 16, and the index finger pocket 12b, it is to be understood that this is only one graphic representation of the myriad of alternate embodiments having alternate substance communication pathway 14 termination points. For example, it may terminate at the distal end of each finger pocket 12b–12d, or may terminate at the distal end of thumb pocket 12a.

Treatment substances are communicated from the treatment substance reservoir 18 via the substance communication pathway to the channel termination point 15. Upon reaching the channel termination point 15, treatment substances are forced out of the substance communication channel 14 through apertures 15a and 15b. The treatment substances are thus applied to the outside of glove body 10, and in particular to the distal end of finger pocket 12b. The substances can be administered to a treatment site by bringing the portion of the glove body 10 with treatment substance applied to its surface into contact with the desired treatment site.

Unlike the glove apparatus disclosed in the prior art, the rectal glove according to the instant invention is particularly suitable for internal use in a mammalian body, rather than external use. The instant rectal glove is preferably embodied in a disposable, tactile material comprising a smooth external surface without any appendages that could potentially cause trauma to internal body surfaces at a treatment site and/or surrounding areas.

Figure 2:
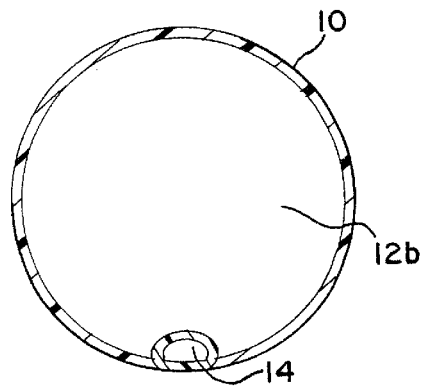
FIG. 2 sets forth a cross sectional view taken along lines 1—1 of FIG. 1.
Figure 3:
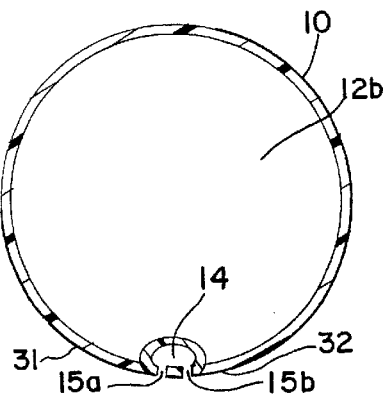
FIG. 3 sets forth a cross sectional view taken along lines 2—2 of FIG. 1.

The features of the present invention may be better understood by viewing FIGS. 2 and 3. FIG. 2 is a cross sectional view of the finger pocket 12b along lines 1—1. At this point in the glove body 10, the substance communication channel 14 is fully embedded within glove body 10. It is to be understood that the substance communication channel is embedded in such a manner to maximize both flexibility of the device and the amount of substance that the doctor can feel through the device, and to minimize any rough edges or other protrusions that may irritate or inflame the treatment and/or surrounding area.

FIG. 3 is a cross sectional view of the finger pocket 12*b* along line 2—2. At this point, the substance communication channel 14 is no longer fully embedded within glove body 10. Treatment substances communicated from the treatment substance reservoir 18 via substance communication pathway 14 may exit through apertures 15*a* and 15*b*. Upon expulsion from the substance communication pathway 14, the treatment substances may be applied to the outer surfaces 31 and 32 of finger pocket 12*b*. The treatment substances can be massaged or rubbed on to a treatment site. In the alternative, the treatment substances can be communicated to the treatment site as the doctor simultaneously rubs or massages the treatment site. In this manner, the doctor can accomplish two beneficial results simultaneously, application of the treatment substance and massage of the treatment site.

Figure 4:
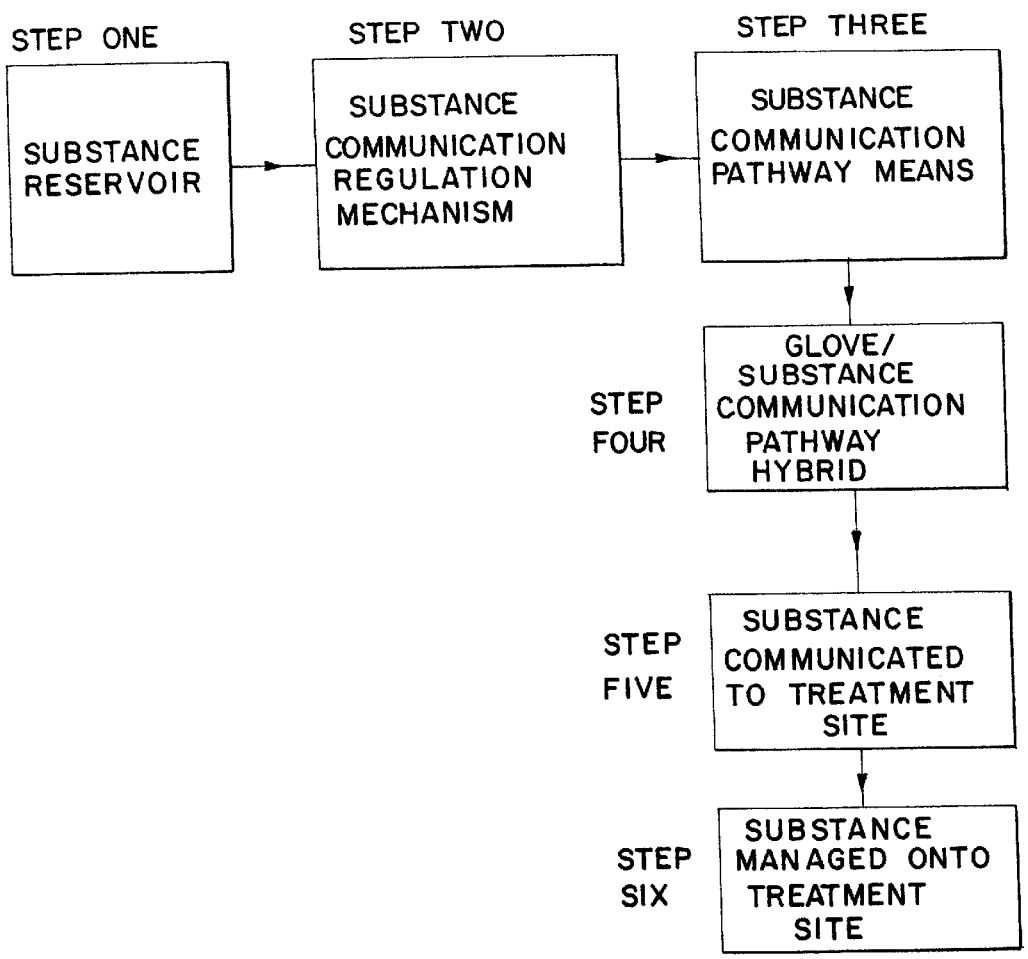
FIG. 4 is a schematic flow-chart depiction in accordance with the present invention.

FIG. 4 is a schematic flow-chart depiction according the present invention. In step one, the desired treatment substance is inserted in the treatment substance reservoir 18. The treatment reservoir 18 can be any size and any material depending on the procedures accomplished according to the present invention. For example, in a standard procedure where medication is massaged into the back of the prostate, the reservoir may be 3 dm$^3$.

In step two, the treatment substance communicated to the substance communication pathway 14 is regulated. This communication may be regulated electrically, mechanically, or manually. As an example of manual regulation, the treatment substance reservoir 18 may be constructed out of a flexible substance such as rubber or a thin polymer. In this embodiment, the doctor can regulate the amount of treatment substance communicated from the treatment substance reservoir 18 to the substance communication pathway 14 and later communicated to the termination point 15 and through apertures 15*a* and 15*b*, by squeezing the treatment substance reservoir. As an example of mechanical regulation, an embodiment of the present invention may include a regulation mechanism between the treatment substance reservoir 18 and substance communication channel 14. In this embodiment, the regulation mechanism may be a computer controlled stopcock, which for example, depending on the substance communication pathway diameter and the viscosity of the treatment substance, can be programmed to only communicate a designated amount of treatment substance from the treatment substance reservoir 18 to substance communication channel 14 based on the amount of time that the stopcock is open.

In step three, the treatment substance is communicated along substance communication pathway 14 from treatment substance reservoir 18 to the glove body 10. The substance communication pathway may be made out of any material that is unreactive with the treatment substance, but preferably should be substantially comprised of a flexible material to prevent any irritation or inflammation at a treatment site and/or surrounding areas. For example, the substance communication pathway may be substantially rubber, latex or a thin polymer.

It is unnecessary for the substance communication pathway to have an unchanging diameter throughout its length. Variations in diameter, however, will lead to variations in the velocity of treatment substance communication between alternate substance communication channels. Therefore, it is to be understood that the present invention for in vivo administration of various substances may be manufactured with substance communication channels 14 having alternatively sized diameters so that the doctor can select the necessary glove depending on the velocity of treatment substance communication necessary for a particular treatment procedure. The present invention may be embodied in a disposable glove and therefore presents an efficient and economical device for treatment substance communications.

In step four, the treatment substance travels along the substance communication pathway 14 embedded in the glove body 10. Several embodiments are readily envisioned which include the substance communication pathway 14—glove body 10 hybrid. For example, the substance communication pathway 14 may be a channel made substantially out of the same material employed in the remainder of the glove body 10. In this embodiment, the channel has an overlayer or outer surface that is superjacent the glove surface 17. In another embodiment, the glove body 10 may include a channel pocket, having an inner and outer surface, which may accommodate the insertion of an extraneous channel such as a tiny rubber or latex catheter. In this embodiment, the glove body 10 serves a housing for the substance communication channel and may be secured to the substance communication channel by any non-toxic temporary adhesive, clip, or other fastener. In this manner, the substance communication channel may be inserted and secured into the pocket within glove body 10 so that its termination end 15 is directly above the aperture in glove body 10 which permits substance communication to the glove surface 17 and later to the treatment site.

In step five, the treatment substance is communicated to the treatment site via apertures 15*a* and 15*b*. The treatment substance is communicated along substance communication channel 14 by the communication regulation mechanism described above. As the treatment substance reaches termination point 15 of the substance communication channel 14, it is forced out apertures 15*a* and 15*b* and onto the surface 17 of finger packet 12*b*. It is to be understood that many embodiments can be readily envisioned employing alternative termination points throughout the glove body and employing alternative sizes, shapes and numbers of apertures near the termination point. In this manner, the velocity and quantity of treatment substance communicated to the glove surface 17 or treatment site may be manipulated to meet the doctor's requirements for particular procedures. For example, for administering medication to the back of a prostate, two parallel horizontally positioned apertures are ideal because the treatment substance must be massaged onto the prostate in different directions and at a slow pace. The treatment substance may be first applied to the glove surface after expulsion from the substance communication channel 14 through apertures 15*a* and 15*b*, or it may be directly applied to the treatment site if the application finger is in contact or near contact with the treatment site.

The rectal glove according to the instant invention may also be employed in application of treatment substances, especially lubricants, to the external and internal anal sphincters as it is being inserted into the rectal cavity. In this manner, the rectal glove may apply one or more substances along the pathway to the prostate or rectum, or may be used to only apply such substances to the pathway in particular. Further, the rectal glove according to the instant invention may be employed to apply different substances throughout the treatment pathway depending on the requirements of the treating doctor. For example, two or more treatment reservoirs could be simultaneously connected to substance communication channel 14. A multi-way valve could be used to control flow of the substrates into channel 14.

In step six, the treatment substance is massaged or rubbed onto the treatment site. This may be accomplished using medical techniques particular to the required procedure.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

It is to be understood that the invention is not limited in its application to the details of construction and the arrangements of the components set forth in the above description or illustrated in the drawings. The invention is capable of other embodiments and of being practiced and carried out in various ways. Also, it is to be understood that the phraseology and terminology employed herein are for the purpose of description and should not be regarded as limiting.

What is claimed is:

1. A substance communication device comprising:
    a fingered glove defining a pocket for receiving a wearer's hand;
    said glove having an aperture at a desired point wherein said desired point is a contact point between said glove and a treatment site;
    a substance reservoir having a volume permitting containment of a medicament; and
    said substance reservoir connected to said glove by a substance transportation channel having a front end terminating at said desired point and having a back end terminating at said substance reservoir.

2. A substance communication device according to claim 1 further comprising a means to regulate the amount of said medicament communicated from said substance reservoir to said channel and from said channel to said desired point.

3. A substance communication device according to claim 1 wherein said glove is constructed of a substantially disposable material.

4. A substance communication device according to claim 1 further comprising means to determine the time and speed that said medicament is communicated to a treatment site.

5. A substance communication device according to claim 1 wherein said glove contains a channel pocket having an inner and outer surface constructed out of the same material as said glove;
    said channel pocket having a volume sufficient to contain said channel.

6. A substance communication device according to claim 1 wherein said substance reservoir contains greater than one substance.

7. A substance communication device according to claim 1 wherein said substance reservoir is interchangeable with another substance reservoir containing an alternative substance.

8. A substance communication device according to claim 1 wherein said channel has at least one aperture substantially near said desired point.

9. A substance communication device according to claim 1 wherein said channel is embedded within said glove.

10. A substance communication device according to claim 1 wherein said channel communicates said medicament along the wrist, palm and index finger regions.

11. A substance communication device according to claim 1 wherein said desired point is near the distal end of the index finger pocket of said glove.

12. A substance communication device according to claim 1 wherein said channel has a means to deliver medicament to said aperture of said glove.

13. A substance communication device according to claim 12 wherein said means substantially comprises at least one oval-shaped aperture.

14. A substance communication device according to claim 1 wherein said front end of said channel substantially comprises at least one aperture;
    said aperture having a substantially geometrical shape.

* * * * *